United States Patent [19]

Graber

[11] Patent Number: 5,190,561
[45] Date of Patent: Mar. 2, 1993

[54] TISSUE AND ORGAN EXTRACTOR

[75] Inventor: John N. Graber, Minneapolis, Minn.

[73] Assignee: Surgical Innovations, Inc., Minneapolis, Minn.

[21] Appl. No.: 644,987

[22] Filed: Jan. 23, 1991

[51] Int. Cl.⁵ ............................................. A61B 17/32
[52] U.S. Cl. ..................... 606/127; 606/114
[58] Field of Search ............... 128/749, 751; 604/133; 606/46, 47, 51, 52, 113, 114, 170, 171, 205, 110, 127; 403/292, 321, DIG. 8

[56] References Cited

U.S. PATENT DOCUMENTS

| | | | |
|---|---|---|---|
| 1,609,014 | 11/1926 | Dowd | 606/114 |
| 1,918,519 | 7/1933 | Clements | 403/321 |
| 3,472,230 | 10/1969 | Fogarty | 606/127 |
| 3,791,387 | 2/1974 | Itoh | 606/113 |
| 3,800,781 | 4/1974 | Zalucki | 128/749 |
| 3,908,661 | 9/1975 | Kramer | 606/127 |
| 4,557,255 | 12/1985 | Goodman | 606/127 |
| 4,633,869 | 1/1987 | Schmieding | 606/170 |
| 4,657,020 | 4/1987 | Lifton | 606/127 |
| 4,739,760 | 4/1988 | Chin et al. | 606/171 |
| 5,057,114 | 10/1991 | Wittich et al. | 606/127 |

Primary Examiner—Max Hindenburg
Attorney, Agent, or Firm—Dorsey & Whitney

[57] ABSTRACT

A tissue and organ extractor is provided for use during laparoscopic surgical procedures. The extractor is generally rod-shaped, having a handle, an elongated shank with a central bore, and a flexible collapsible cone-shaped terminal end. The shank extends continuously between the handle and the cone-shaped terminal end. The cone-shaped end is the intra-abdominal end of the instrument and includes a generally circular open end. The handle includes a locking lever for locking a grasping instrument, which might be used to grasp tissue or organs, securely in place in relation to the extractor.

In use, the surgeon inserts the extractor through a cannula and, using the grasping instrument, manipulates a tissue or organ into the open-ended, cone-shaped terminal end. The instrument used to manipulate the tissue may be locked into place in the shank of the extractor, and the extractor, instrument and tissue contained in the extractor may be removed from the abdominal cavity through the cannula. As it is being removed, the flexible cone-shaped end of the extractor envelops and compresses the tissue contained therein.

5 Claims, 4 Drawing Sheets

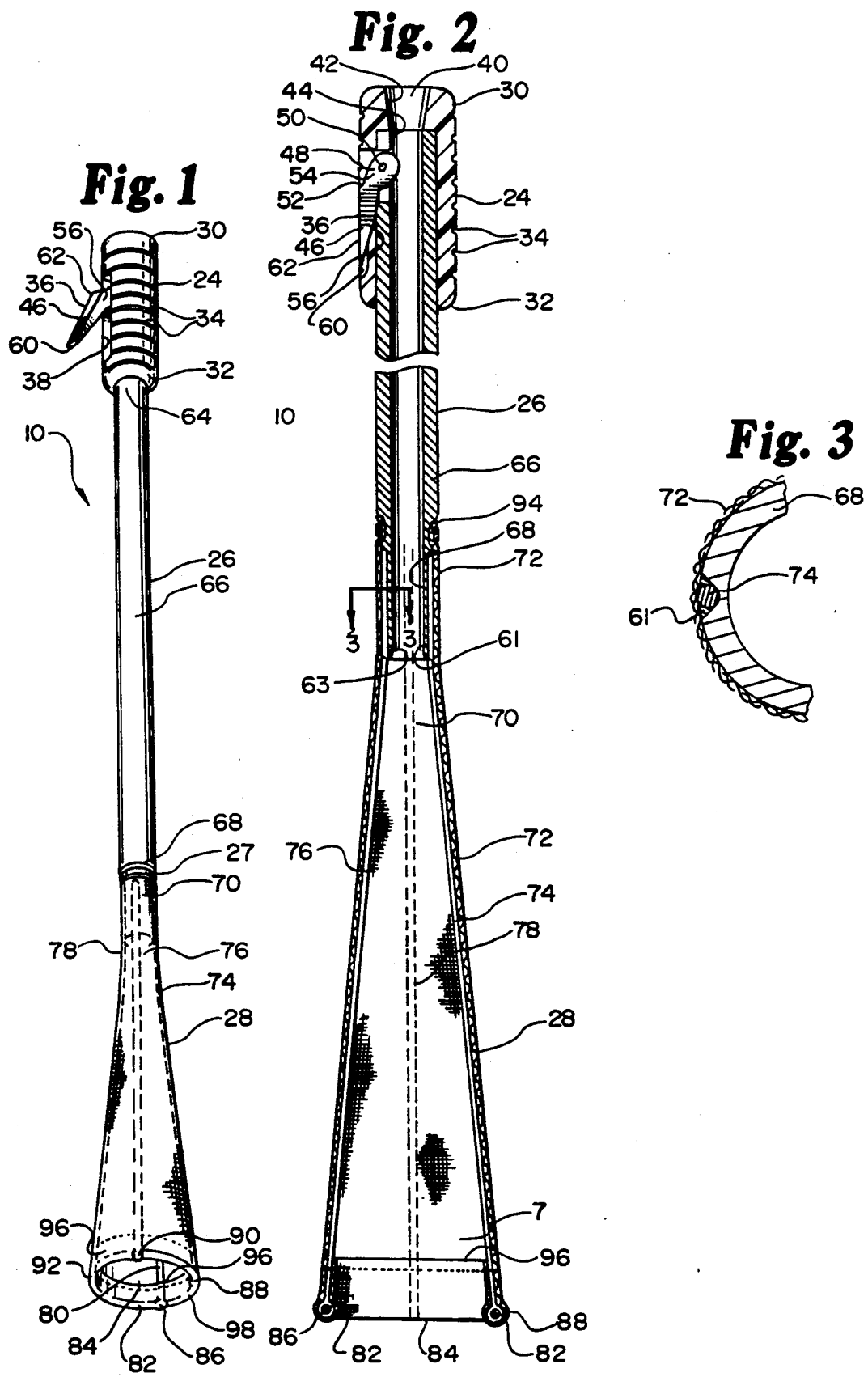

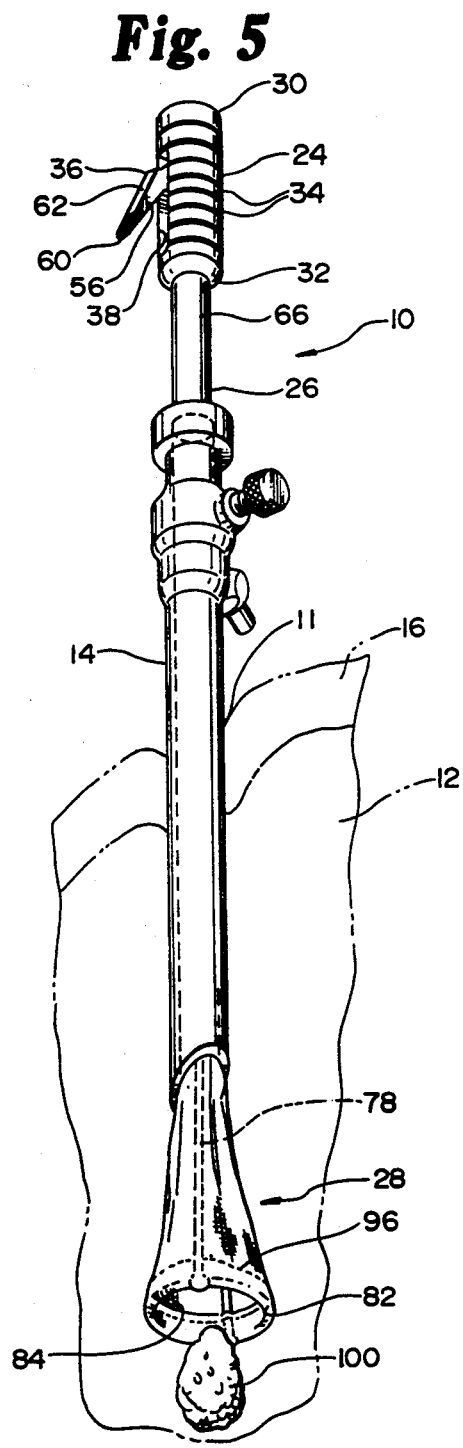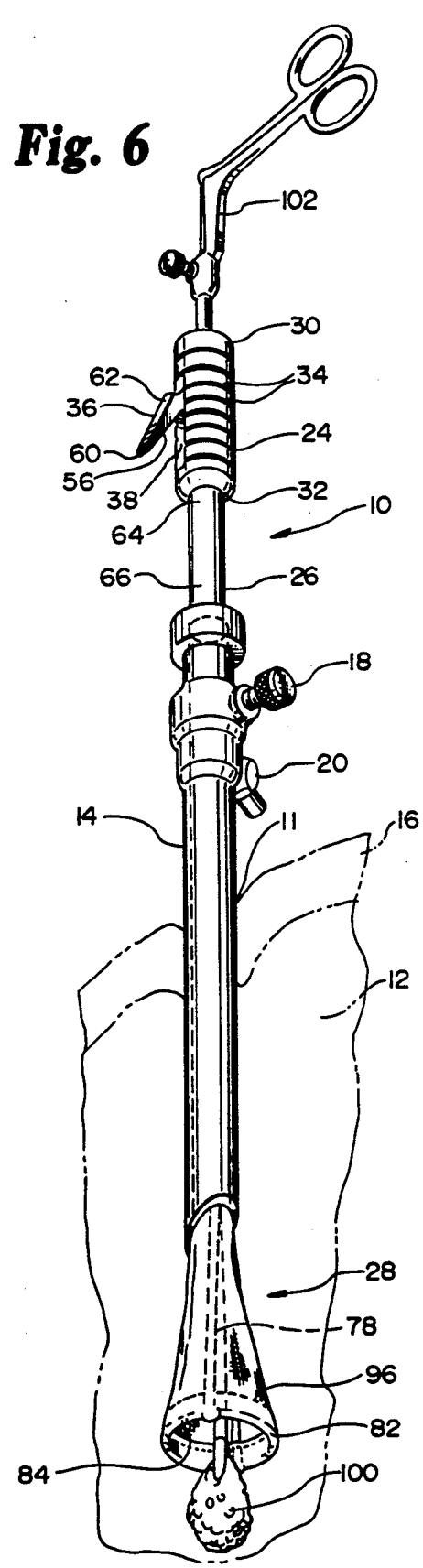

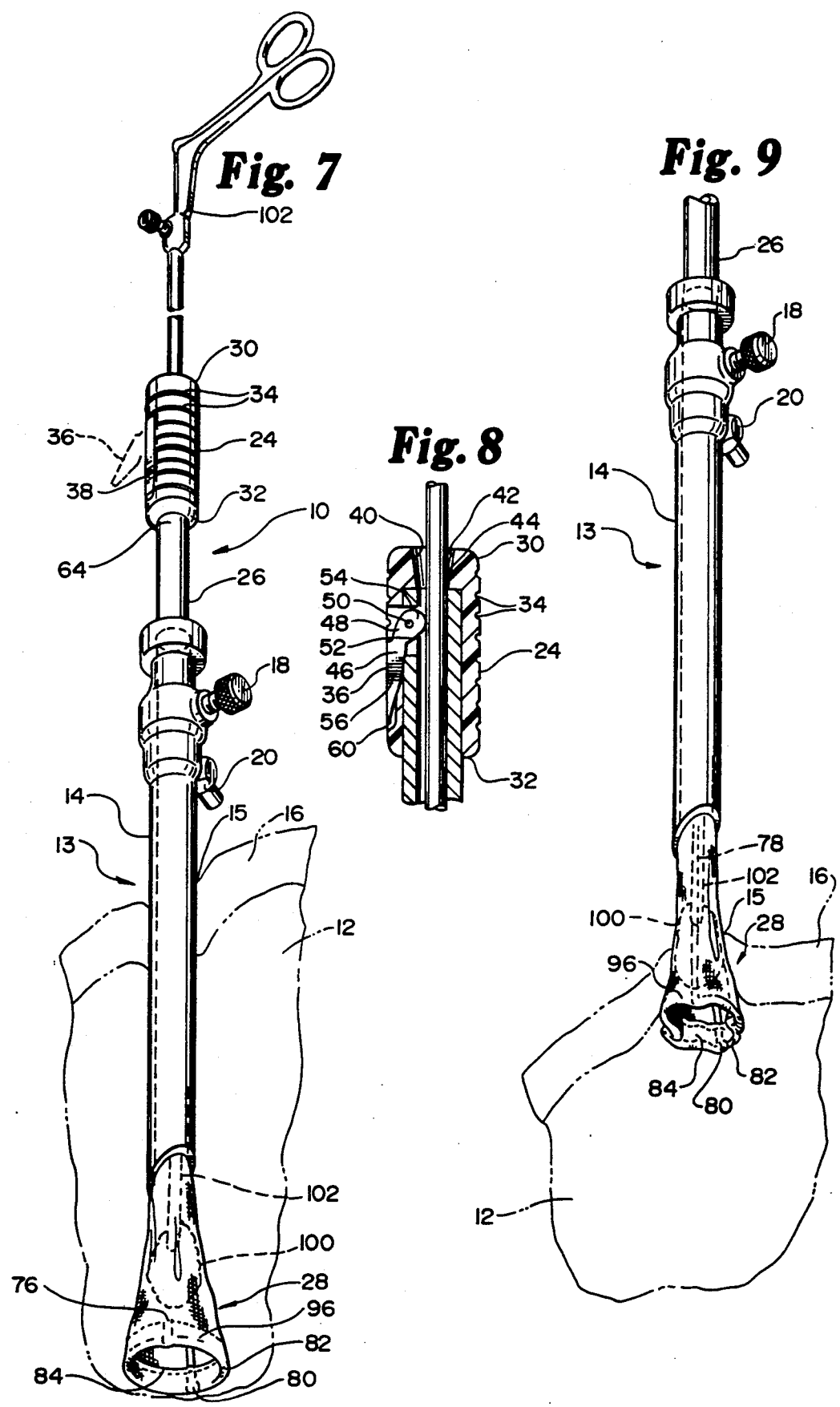

TISSUE AND ORGAN EXTRACTOR

TECHNICAL FIELD

This invention relates generally to the field of instruments used in surgical procedures. In particular, it relates to an instrument for use during laparoscopic surgical procedures wherein the instrument may be used for encompassing an organ or tissue as it is graspably removed from a patient through a small puncture orifice.

BACKGROUND ART

Laparoscopy is noninvasive, nontraumatic surgery that involves visualizing the interior of the abdominal cavity using an illuminating optical instrument, a laparoscope, that is placed through a puncture orifice in the abdominal wall. Laparoscopic procedures have value as a diagnostic and operative tool for general surgery, as well as for gynecological surgery wherein such procedures are widely used. As physicians specializing in other fields have begun to recognize the advantages of laparoscopic surgery, the need for providing surgical tools especially adapted for general laparoscopic procedures has increased.

Instruments used during laparoscopic procedures are introduced into the abdominal cavity through a device known as a "trocar." A trocar comprises a cannula or trocar sleeve (a hollow sheath or sleeve with a central lumen) into which fits an obturator, a solid metal rod with an extremely sharp three-cornered tip used for puncturing the muscle. The obturator is withdrawn after the instrument has been pushed in the abdominal cavity. The trocar sleeve remains in the body wall throughout the surgical procedure and various instruments and surgical tools used during laparoscopic procedures are introduced in the abdomen through this sleeve. Trocars are available in different sizes to accommodate various instruments.

The advantages of laparoscopic surgery include: avoiding unnecessary general surgery by performing the procedure on an outpatient basis; providing the surgeon the opportunity for viewing intra-abdominal viscera without laparotomy, a large incision made in the abdominal wall; using small puncture wounds as opposed to large incisions, lessening the danger of traumatic injury to delicate intraabdominal tissues; determining incision sites for laparotomies when such incisions are appropriate; reducing both patient and insurer medical costs by shortening hospital stays; and reducing postoperative patient discomfort with recovery times measured in days as opposed to weeks.

Laparoscopic instruments for gall bladder surgery are known in the prior art. Existing laparoscopic instruments are inserted through the trocar sleeve and are used to grasp the tissue or organ to be removed from a patient's abdominal cavity. However, while the prior art devices are capable of extracting the tissue or organ from the abdominal cavity of a patient, their design has limited their use in certain applications.

One of the problems associated with existing instruments is that when dealing with soft tissue or organs, the tissue or organ can tear especially as the surgeon removes the tissue or organ through the trocar sleeve. If parts of tissue are left in the abdominal cavity or if the contents of an infected organ are released into the abdominal cavity, infection may result requiring the surgeon to use laparotomy to remove the tissue or organ. This would defeat the purpose and advantages of laparoscopic surgery enumerated above by necessitating a longer hospital stay for the patient, increased expense for the patient and his or her insurer, as well as a lengthy post-operative recovery period. A tissue and organ extractor that could be used to safely and completely extract tissue and organs from the abdominal cavity of a patient without tearing and that could be used in a wide variety of laparoscopic procedures would provide a decided advantage over the prior art.

SUMMARY OF THE INVENTION

The problems outlined above are in large measure solved by the tissue extractor in accordance with the present invention. While the instrument in accordance with the present invention is adapted especially for removal of the gall bladder, it is suitable for use in any laparoscopic procedure wherein delicate tissues or organs must be removed from the abdominal cavity during surgery.

The tissue and organ extractor hereof is generally rod shaped, having a handle, an elongated central shank, and a flexible cone-shaped terminal end. The shank extends continuously between the handle and the cone-shaped terminal end. The cone-shaped end is the intra-abdominal end of the instrument, and includes a generally circular portion at its lowermost rim. The circular portion houses a flexible cable for easily removing the instrument and its organ or tissue contents from the abdominal cavity of the patient. The handle end includes a locking lever for locking a grasper instrument, which grasps the tissue or organ securely in place in relation to the tissue and organ extractor.

In use, the tissue and organ extractor is inserted through the trocar sleeve, placed in close proximity to the organ or tissue and is locked into place by set screws located on the trocar sleeve. The surgeon inserts graspers through the tissue and organ extractor and grasps the tissue or organ with the graspers. The tissue or organ is then drawn inside the cone-shaped terminal end of the tissue and organ extractor. The grasper is then locked into placed in relation to the tissue and organ extractor by the locking lever. The grasper, the tissue and organ extractor, and the trocar sleeve are then removed from the patient's abdomen through the puncture orifice. As the instruments are removed from the abdominal cavity, the flexible cone-shaped end of the tissue extractor envelops and compresses the tissue thus preventing the traumatic manipulation of the organ or tissue as it passes through the puncture orifice making the laparoscopic procedure safer for the patient and more efficient for the surgeon.

BRIEF DESCRIPTION OF THE DRAWINGS

FIG. 1 is a perspective view of the tissue and organ extractor in accordance with the present invention;

FIG. 2 is a longitudinal cross sectional view of the extractor;

FIG. 3 is a fragmentary sectional view taken along line 3—3 of FIG. 2;

FIG. 5 is similar to FIG. 4 but with the extractor fully inserted into the abdomen;

FIG. 6 is similar to FIG. 5 but with tissue to be extracted from the patient's abdominal cavity graspably engaged by the grasper jaws of a grasper;

FIG. 7 is similar to FIG. 6 but with the tissue drawn up inside the tissue and organ extractor and the locking lever of the extractor in accordance with the present invention locking the grasper into place;

FIG. 8 is a sectional view taken along line 8—8 of FIG. 7;

FIG. 9 is a fragmentary perspective view of the tissue and organ extractor in accordance with the present invention depicting the final stages of operation as the tissue is extracted through the puncture orifice in the abdominal wall.

DETAILED DESCRIPTION OF THE INVENTION

Figure 4:
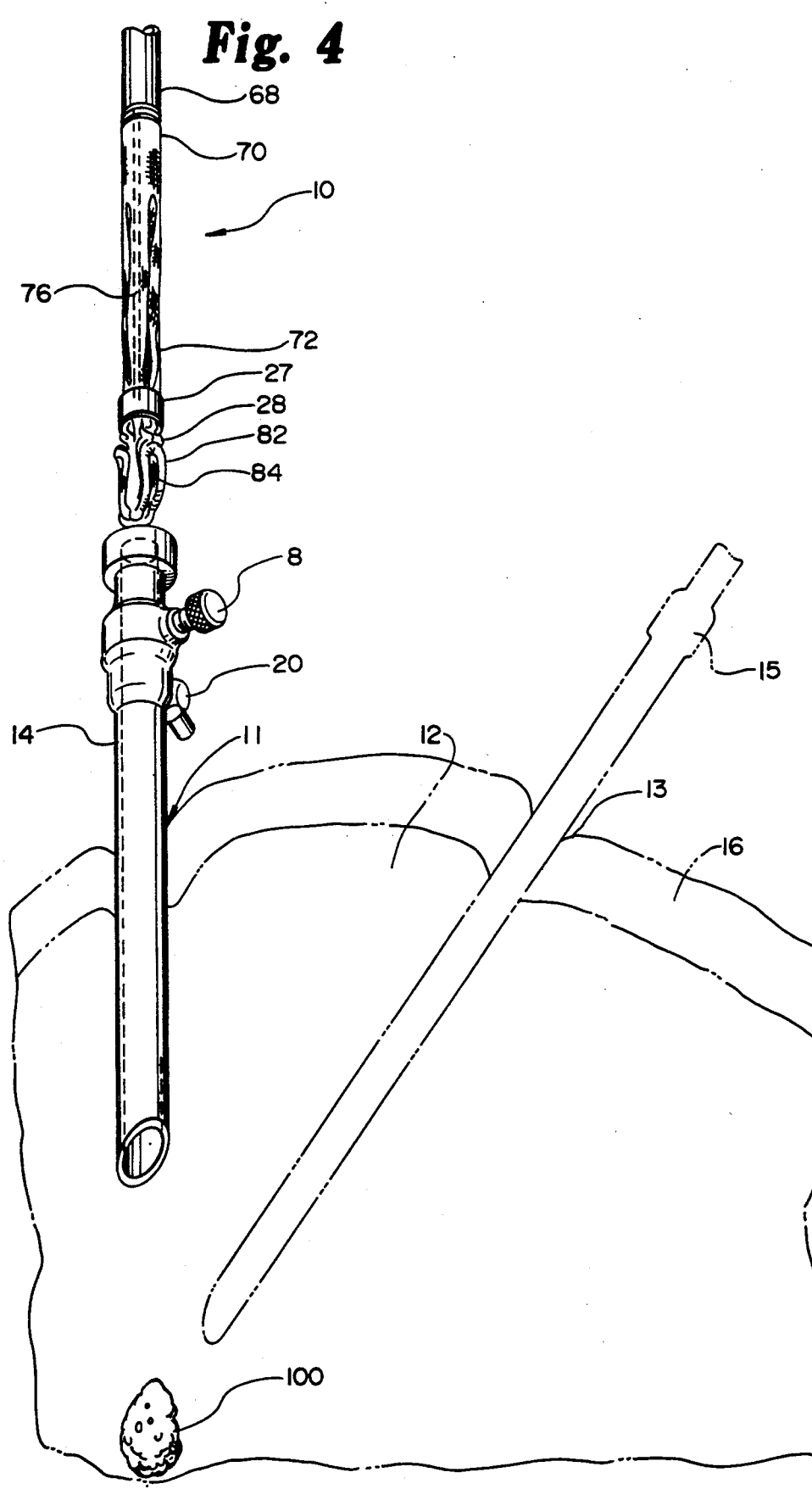
FIG. 4 is a fragmentary perspective view of the extractor in accordance with the present invention positioned for insertion into a trocar sleeve, with phantom lines depicting the intra-abdominal region of a patient and an auxiliary laparoscopic device.

FIG. 4 depicts the tissue and organ extractor 10 in accordance with the present invention being inserted into the intra-abdominal cavity 12 of a patient. Puncture orifices 11, 13 are made in the abdominal wall 12 of the patient by the insertion of a trocar through the abdominal wall 16 and into the intra-abdominal cavity 12. Once the surgeon uses the sharp tipped obturator (not shown) to make puncture orifices 11, 13, the obturator is removed and trocar sleeves 14, 15 are left in the patient. A laparoscope (not shown) is introduced into the abdominal cavity 12 through trocar sleeve 15 depicted in phantom lines in FIG. 4. The laparoscope, an illuminating optical instrument, is used to visualize the interior of the abdominal cavity 12.

Trocar sleeve 14 provides the pathway for laparoscopic instruments to be inserted into the intra-abdominal cavity 12. Various instruments introduced into the intra-abdominal cavity 12 of the patient through trocar sleeve 14, may be locked into place by set screws 18, 20 thereby freeing the surgeon's hands for other tasks. An auxiliary trocar sleeve (not shown) may be used to insert additional instruments into the intra-abdominal cavity 12.

Referring to FIGS. 1 and 2, the tissue and organ extractor 10 is generally rod shaped and broadly includes a hand-graspable handle 24, an elongated hollow central shank 26, ring 27 and a generally cone-shaped terminal end 28.

FIGS. 2 and 8 provide additional detail regarding the handle 24. Specifically, the handle 24 has a larger outer diameter than the shank 26, which precludes the extractor 10 from entering the trocar sleeve 14 beyond a certain point. Handle 24 includes upper end 30, bottom end 32, circumferentially cut grooves 34, locking lever 36, recess 38 and hollow chamber 40. Grooves 34 are designed to permit the surgeon to grasp and manipulate the instrument more easily. Chamber 40 includes top portion 42 and lower portion 44. The outer diameter of chamber 40 is the same as the inner diameter of hollow shank 26.

Recess 38 is generally rectangularly shaped and is disposed in handle 24. Locking lever 36 is received in recess 38. The locking lever 36 includes pull 46, cam 48 and pivot 50. Pivot 50 is connected to the crown 52 of shank 26. Lever 36 includes head 54, generally planar opposed side portions 56, 58, finger-tip grasping end 60 and a generally planar top surface 62. Lever 36 is generally shorter in length than recess 38, thereby permitting the surgeon to easily grasp finger-tip grasping end 60. Handle 24 is made from an elastomeric synthetic resin or some other suitable hand graspable material.

The hollow shank 26 has a generally central longitudinal axis and includes proximal end 64, elongated cylindrical body 66 and tail 68. The proximal end 64 is received within handle 24 and extends from the lower portion 44 of chamber 40 to the bottom end 32 of handle 24. Cylindrical body 66 is generally rigid and extends from the bottom end 32 of handle 24 to tail 68. A plurality of longitudinally cut grooves 61, 63, 65, 67 surround the circumference of tail 68 in a spaced apart relationship.

Ring 27 is positioned over neck 70. The inner diameter of ring 27 is the same as the outer diameter of neck 70. The outer diameter of ring 27 is larger than the inner diameter of trocar sleeve 14 which precludes it from entering trocar sleeve 14 beyond a certain point.

Cone-shaped terminal end 28 includes neck 70, covering 72, a plurality of elongated wires 74, 76, 78, 80, cable 82, and mouth 84. Terminal end 28 tapers gradually to form trumpet shaped mouth 84. The degree of taper from mouth 84 to neck 70 may be varied depending on the diameter of the tissue or organ to be removed from abdominal cavity 12. The inner diameter of neck 70 is the same as the inner diameter of cylindrical body 66.

Referring to FIGS. 2 and 3, generally cylindrical elongated wires 74, 76, 78, 80 shown in phantom lines are flexible and extend generally outwardly from tail 68 to mouth 84 and include eye ends 86, 88, 90, 92. Wires 74, 76, 78, 80 are received in grooves 61, 63, 65, 67. Web 72 covers and is attached to wires 74, 76, 78, 80 by threading, heat pressing or other suitable means. Web 72 holds wires 74, 76, 78, 80 flush against grooves 61, 63, 65, 67 but is is not beyond the scope of the present invention that wires 74, 76, 78, 80 are held flush against grooves 61, 63, 65, 67 by soldering, plastic adhesive, resin or other suitable means. Wires 74, 76, 78, 80 exert an outward bias on Web covering 72 providing tensile strength to covering 72.

Web 72 is made from a sturdy waterproof, stain resistant fabric such as treated sail cloth or duck cloth but it is not beyond the scope of the present invention that other suitable materials be used. Web 72 includes a first edge 94 and a second edge 96. First edge 94 is connected to the tail 68 of cylindrical body 66 by screws, snaps or other suitable means.

Cable 82 is received through eye ends 86, 88, 90, 92 to form a generally circular circumference at mouth 84. Web 72 extends over and covers cable 82. Web 72 is joined to itself at second edge 96 by threading, heat pressing, plastic adhesive or other suitable means. The convex surface of cable 82 presents a rounded peripheral lower margin 98 to cone 28.

Referring to FIG. 4 an auxiliary trocar sleeve (not shown) is introduced into abdominal cavity 12. A laparoscope (not shown) is introduced into abdominal cavity 12 through the trocar sleeve. The laparoscope, an illuminating optical instrument, is used to visualize the interior of the abdominal cavity 12. A camera (not shown) is placed over the eyepiece of the laparoscope and the procedure is monitored on a television screen. Trocar 14 and an additional auxiliary trocar sleeve 22 are introduced into the abdominal cavity 12 to provide the passageway for the instruments necessary to perform any particular laparoscopic surgical procedure wherein the present invention may be utilized. The cone-shaped terminal end 28 of the tissue and organ extractor 10 in accordance with the present invention is collasped from its extended organ receiving configuration to a collasped organ encompassing configuration by lowering ring 27 over Web 72. The tissue and organ extractor 10 is then introduced through trocar sleeve 14 into abdominal cavity 12.

Referring to FIGS. 5, 6, 7 and 9, as the the tissue and organ extractor 10 is introduced into abdominal cavity 12, it is placed in close proximity to the tissue or organ 100 to be removed. Tissue and organ extractor 10 is locked into place by set screws 18 and 20 located on trocar sleeve 14. Graspers 102 are introduced into abdominal cavity 12 through chamber 40, hollow body 66, and cone-shaped terminal end 28. The surgeon manipulates graspers 102 to grasp the edge of tissue or organ 100 and draws the tissue or organ 100 into the mouth 84 of terminal end 28.

Using locking lever 36, the surgeon locks graspers 102 and tissue 100 in place inside terminal end 28. The surgeon then removes the entire structure, trocar 14, tissue and organ extractor 10, graspers 102 and tissue 100 through puncture orifice 11 in abdominal cavity 12. As the entire structure is being removed through puncture orifice 11, flexible cone-shaped terminal end 28 collapses from an extended configuration to a collapsed configuration thereby compressing and enveloping tissue or organ 100. Mouth 84 constricts as it passes through puncture orifice 11 and lip 98 forms a seal preventing the tissue or organ 100 or parts that break off thereof from re-entering the abdominal cavity 12.

I claim:

1. A tissue and organ extractor for use in laparoscopy along with auxiliary surgical instruments, said extractor for encompassing and extracting tissues, organs or the like from a body cavity during a laparoscopic surgical procedure and comprising:
   a generally tubular, elongated rod-shaped shank having a handle end and a working end, said shank having a longitudinal bore extending the length of said shank, said bore for receiving said auxiliary instruments;
   a flexible collapsible generally cone-shaped encompassing means for substantially entirely encompassing and compressing said tissue, organ or the like during the extraction thereof from said body cavity, said encompassing means operably coupled to said working end of said shank end and including an open end; and
   handle means for holding said extractor, said handle means being at said handle end of said shank and including a locking means for engaging and securing one of said auxiliary surgical instruments in fixed relationship to said encompassing means while said one of said auxiliary surgical instrument is in said bore.

2. The extractor according to claim 1, wherein said encompassing means comprises a substantially impermeable fabric-like cone-shaped web having a small end and a relatively larger open end, said small end connected to said working end of said shank, said web being collapsibly supported in said cone shape by a plurality of wires operably connected to said working end of said shank, said wires extending generally outwardly away from said working end at an angle thereto and exerting an outward bias against said cone-shaped web.

3. The extractor according to claim 2, wherein said locking means includes a lever having a finger graspable end and a cam end, said lever being pivotally connected to said shank whereby it is movable into direct engagement with one of said auxiliary instruments in said bore.

4. A tissue and organ extractor for use in laparoscopy along with auxiliary surgical instruments, said extractor for encompassing and compressing tissues, organs or the like for the extraction thereof from a body cavity and comprising:
   a tubular, elongated rod-shaped shank having a handle end and a working end, said shank having a central longitudinal bore extending the length of the shank, said bore for receiving said auxiliary instruments;
   a flexible, collapsible generally cone-shaped terminal end connected to said working end of said shank and comprising a plurality of elongated wires each having a first end connected to said shank, said first ends defining an extractor neck with a diameter substantially equal to the diameter of said shank, and a second end, said second ends defining a constrictable open trumpet-shaped mouth, said wires tapering outwardly from said neck to said mouth, and a substantially waterproof fabric web covering and supported by said wires; and
   a handle mounted at the handle end of said shank, extending around said shank and having a diameter greater than the diameter of the shank, said handle including a lock for securing an auxiliary instrument in said bore, said lock comprising a generally rectangular recess in said handle and shank and a locking lever pivotally mounted in said recess, said locking lever having an auxiliary instrument contacting cam head extending variably into said bore.

5. The extractor according to claim 4, wherein said second ends of said wires carry eyes for receiving a flexible cable means for forming a generally circular circumference of said constrictable, open trumpet-shaped mouth.

* * * * *